US011344262B2

(12) United States Patent
Senegas et al.

(10) Patent No.: US 11,344,262 B2
(45) Date of Patent: May 31, 2022

(54) AUTOMATED COMPUTATION OF TRIGGER DELAY FOR TRIGGERED MAGNETIC RESONANCE IMAGING SEQUENCES

(71) Applicant: KONINKLIJKE PHILIPS N.V., Eindhoven (NL)

(72) Inventors: Julien Senegas, Hamburg (DE); Sascha Krueger, Hamburg (DE)

(73) Assignee: Koninklijke Philips N.V., Eindhoven (NL)

(*) Notice: Subject to any disclaimer, the term of this patent is extended or adjusted under 35 U.S.C. 154(b) by 356 days.

(21) Appl. No.: 16/468,734

(22) PCT Filed: Dec. 11, 2017

(86) PCT No.: PCT/EP2017/082237
§ 371 (c)(1),
(2) Date: Jun. 12, 2019

(87) PCT Pub. No.: WO2018/108821
PCT Pub. Date: Jun. 21, 2018

(65) Prior Publication Data
US 2020/0093443 A1 Mar. 26, 2020

Related U.S. Application Data

(60) Provisional application No. 62/433,835, filed on Dec. 14, 2016.

(51) Int. Cl.
*A61B 5/00* (2006.01)
*G01R 33/567* (2006.01)

(52) U.S. Cl.
CPC .......... *A61B 5/7292* (2013.01); *A61B 5/7282* (2013.01); *A61B 5/7289* (2013.01); *G01R 33/5673* (2013.01); *G01R 33/5676* (2013.01)

(58) Field of Classification Search
None
See application file for complete search history.

(56) References Cited

U.S. PATENT DOCUMENTS 8,971,602 B2\* 3/2015 Glaser .............. G01R 33/56358
382/131
2005/0113672 A1 5/2005 Salla et al.
(Continued)

FOREIGN PATENT DOCUMENTS

JP 2014161566 A 9/2014

OTHER PUBLICATIONS

Question and Answers in MRI—Intro to Gating/Triggering. Elster LLC., Feb. 11, 2016 (Year: 2016).\*
(Continued)

*Primary Examiner* — Yi-Shan Yang

(57) ABSTRACT

A magnetic resonance (MR) imaging device repeatedly executes a navigator pulse sequence to generate navigator data in image space as a function of time, and a motion signal of an anatomical feature that moves with a physiological cycle as a function of time is extracted from the navigator data. A concurrent physiological signal as a function of time is generated by a physiological monitor concurrently with the repeated execution of the navigator pulse sequence. A gating time offset is determined by comparing the motion signal of the anatomical feature as a function of time and the concurrent physiological signal as a function of time. The MR imaging device performs a prospective or retrospective gated MR imaging sequence using gating times defined as occurrence times of gating events detected by the physiological monitor modified by the gating time offset.

18 Claims, 3 Drawing Sheets

(56) References Cited

U.S. PATENT DOCUMENTS

| | | | |
|---|---|---|---|
| 2005/0113702 A1 | 5/2005 | Salla et al. | |
| 2006/0183999 A1* | 8/2006 | Lorenz | A61B 5/055 600/410 |
| 2010/0308823 A1 | 12/2010 | Sugiura | |
| 2012/0259202 A1* | 10/2012 | Zheng | A61B 5/055 600/413 |
| 2014/0073902 A1 | 3/2014 | Popescu | |
| 2014/0292331 A1 | 10/2014 | Fautz | |
| 2015/0157277 A1* | 6/2015 | Goto | A61B 5/055 600/413 |
| 2016/0198970 A1 | 7/2016 | Liu et al. | |
| 2016/0377693 A1* | 12/2016 | Pednekar | G01R 33/385 324/322 |

OTHER PUBLICATIONS

International Search Report PCT/EP2017/082237 dated Apr. 4, 2018.

* cited by examiner

AUTOMATED COMPUTATION OF TRIGGER DELAY FOR TRIGGERED MAGNETIC RESONANCE IMAGING SEQUENCES

CROSS REFERENCE TO RELATED APPLICATIONS

This application is a U.S. national phase application of International Application No. PCT/EP2017/082237 filed on Dec. 11, 2017, which claims the benefit of U.S. Provisional Application Ser. No. 62/433,835 filed on Dec. 14, 2016 and is incorporated herein by reference.

FIELD

The following relates generally to the medical imaging arts, gated medical imaging arts, magnetic resonance imaging arts, and related arts.

BACKGROUND

Where imaging artefacts due to respiration or cardiac pulsation in magnetic resonance (MR) imaging scans are of concern, a physiology sensor may be used during MR examinations to measure the relevant physiology signal and compute a physiology curve. This signal can be used during imaging to trigger the data acquisition or for gating. The physiological sensor may, for example, measure respiratory motion using an air-filled belt attached to a pressure sensor, or an optical camera can track the motion of a body part or of a dedicated marker and the respiratory signal derived from the imaged motion. Cardiac pulsation is often measured using a pulse pickup photoplethysmography (PPG) sensor or an electrocardiogram (ECG) device. Alternatively, optical camera systems measuring the variation of reflected light over a skin area can be used to monitor cardiac activity. The respiration or cardiac signal measured by such a physiological sensor is a surrogate for the motion of the internal organs being imaged by the MR imaging.

The following discloses new and improved systems and methods.

SUMMARY

In one disclosed aspect, a gating device is disclosed for a magnetic resonance (MR) imaging device. The gating device includes a physiological monitor, an electronic processor, and a non-transitory storage medium that stores a navigator pulse sequence, a gated MR imaging sequence, and instructions readable and executable by the electronic processor to perform a gated MR imaging method. The method includes: operating the MR imaging device to repeatedly execute the navigator pulse sequence to generate navigator data in image space as a function of time; extracting a motion signal of an anatomical feature as a function of time from the navigator data; concurrently with operating the MR imaging device to repeatedly execute the navigator sequence, acquiring a concurrent physiological signal as a function of time generated by the physiological monitor; determining a gating time offset by comparing the motion signal of the anatomical feature as a function of time and the concurrent physiological signal as a function of time; and operating the MR imaging device to perform the gated MR imaging sequence using gating times defined as occurrence times of gating events detected by the physiological monitor modified by the gating time offset.

In another disclosed aspect, a non-transitory storage medium stores a navigator pulse sequence, a gated magnetic resonance (MR) imaging sequence, and instructions readable and executable by an electronic processor to perform a gated MR imaging method comprising: operating an MR imaging device to repeatedly execute the navigator pulse sequence to generate navigator data in image space as a function of time; extracting a motion signal of an anatomical feature as a function of time from the navigator data; concurrently with operating the MR imaging device to repeatedly execute the navigator sequence, acquiring a concurrent respiratory or cardiac cycling signal as a function of time generated by a respiratory or cardiac monitor; determining a gating time offset by comparing the motion signal of the anatomical feature as a function of time and the concurrent respiratory or cardiac cycling signal as a function of time; and operating the MR imaging device to perform the gated MR imaging sequence using gating times defined as occurrence times of gating events detected by the respiratory or cardiac monitor modified by the gating time offset.

In another disclosed aspect, a gated magnetic resonance (MR) imaging method comprises: repeatedly executing a navigator pulse sequence using an MR imaging device to generate navigator data in image space as a function of time; extracting a motion signal of an anatomical feature as a function of time from the navigator data; concurrently with operating the MR imaging device to repeatedly execute the navigator sequence, acquiring a concurrent respiratory cycling signal as a function of time generated by a respiratory monitor; determining a gating time offset by comparing the motion signal of the anatomical feature as a function of time and the concurrent respiratory cycling signal as a function of time; and operating the MR imaging device to perform a gated MR imaging sequence using gating times defined as occurrence times of gating events detected by the respiratory monitor modified by the gating time offset.

One advantage resides in providing physiological gating with improved fidelity to a desired state of the internal organ(s) being imaged.

Another advantage resides in providing gated MR imaging more accurately targeting a desired state of the internal organ(s) being imaged.

Another advantage resides in providing gated MR imaging with user selection of the desired state of the internal organ(s) isolated by the gating.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

An implicit assumption made during typical gated MR imaging is that the physiological signal (e.g. respiration or cardiac cycling signal) measured by a physiological sensor is closely correlated with, and "in phase with", the dominant motion of the internal organs and that motion state of the internal organ, such as end-expiration or end-inspiration (or end-diastole and end-systole). In some gating devices, a pre-set or operator-set constant time delay can be added to the physiological signal gating event detected within each respiratory or cardiac cycle measured by the physiological device. It is recognized herein that these assumptions may be in error for a particular patient or a particular MR imaging examination. In gating approaches disclosed herein, for optimal image quality the gating time offset is set individually for each patient and each MR imaging examination.

Figure 1:
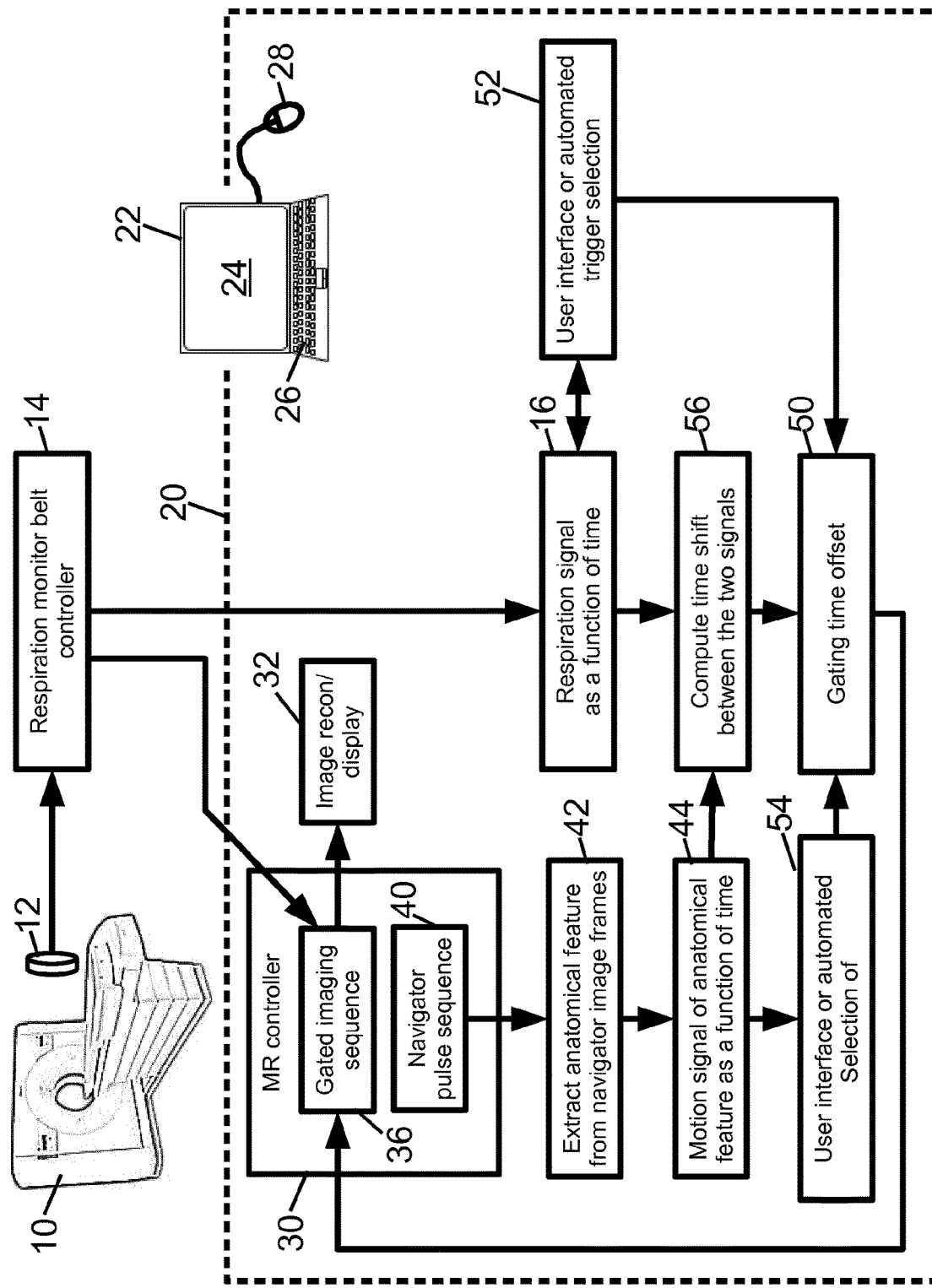
FIG. 1 diagrammatically illustrates a magnetic resonance (MR) imaging device including respiratory gating as disclosed herein.

With reference to FIG. 1, a gated magnetic resonance (MR) imaging system includes an MR imaging device 10, which may by way of non-limiting illustration comprise an Ingenia™ MR imaging device available from Koninklijke Philips N.V., Eindhoven, the Netherlands. A physiological monitor 12 is provided to monitor a physiological signal which is used for the gating. In the illustrative embodiments, the physiological monitor 12 is a respiratory monitor in the form of an air-filled belt attached to a pressure sensor, such that as the patient inhales the pressure in the air-filled belt increases and as the patient exhales the pressure decreases, so that the pressure as a function of time is a representation of the patient respiration as a function of time. (While the term "patient" is used herein for brevity, it will be understood that the MR imaging subject may be a hospital patient, an out-patient, a human subject receiving a medical screening, an athlete or other person receiving a medical clearance including an MR imaging examination, or so forth). The illustrative belt-based respiratory monitor 12 is merely an example, and it will be understood that the respiratory monitor may be chosen to monitor another chosen physiological variable used for the gating. As another example, the physiological monitor may be an electrocardiographic (ECG) device monitoring cardiac cycling—such a physiological monitor is suitable for cardiac gating. The physiological monitor 12 includes or is connected with a physiological monitor controller 14, e.g. an electronic processor connected to read the pressure sensor and output an analog or digital pressure reading in the illustrative belt-based respiratory monitor 12, or an ECG controller in the case of an ECG-based cardiac monitor. The output of the physiological monitor 12, 14 is a physiological signal (e.g. respiration signal) 16 as a function of time.

An electronic processor 20 is programmed to perform various functions as disclosed herein. The illustrative electronic processor 20 is embodied as a computer 22 having a display 24 and at least one user input device (e.g. illustrative keyboard 26 and mouse 28, and/or a touch-sensitive overlay of the display 24 or so forth). More particularly, a non-transitory storage medium (not shown) is provided which stores instructions readable and executable by the electronic processor 20 to perform the disclosed various functions. The non-transitory storage medium may, by way of non-limiting example, include a hard disk drive or other magnetic storage medium; an optical disk or other optical storage medium; a solid state drive (SSD) or other electronic storage medium; various combinations thereof; or so forth. The electronic processor 20 implements an MR controller 30 that controls the MR imaging device 10 to perform MR imaging data acquisition, and implements MR image reconstruction and display processing 32, e.g. performing a Fourier reconstruction or other MR image reconstruction to convert acquired k-space MR imaging data to an image in image space and operating the display 24 to display the reconstructed image.

With continuing reference to FIG. 1, a gated MR imaging sequence 36 is stored on a non-transitory storage medium (e.g. the same non-transitory storage medium storing instructions read and executed by the electronic processor 20). Additionally, a navigator pulse sequence 40 is stored on the non-transitory storage medium. The MR controller 30 is programmed to operate the MR imaging device 10 to perform the gated MR imaging sequence 36 using gating times defined as occurrence times of gating events detected by the physiological monitor 12, 14 modified by a gating time offset determined, as disclosed herein, using the navigator pulse sequence 40.

The navigator pulse sequence 40 is a fast MRI sequence that generated MR data (e.g. k-space samples) that can be converted to image space. The navigator pulse sequence 40 can be a fast two-dimensional (2D) or three-dimensional (3D) imaging sequence that acquires a 2D or 3D navigator image, respectively. Alternatively, the navigator pulse sequence 40 can be one or more one-dimensional (1D) pencil beam navigators that acquire one or more 1D navigator data set in image space. The navigator pulse sequence 40 is generally designed to produce a 1D, 2D, or 3D image dataset that intersects an anatomical feature having motion corresponding to the motive physiology that is the basis of the gating. For example, in the case of respiratory-gated MR imaging, a suitable anatomical feature is a thoracic diaphragm boundary or a liver boundary, as these boundaries are expected to move with the respiratory cycle. The thoracic diagram boundary moves since contraction and consequent movement of the thoracic diaphragm provides motive force for inspiration. The liver boundary is expected to move with the respiratory cycle since the liver is close to, and moves with, the thoracic diaphragm. Other anatomical features may instead be used, e.g. a selected rib of the ribcage. In the case of cardiac-gated MR imaging, a suitable anatomical feature whose movement may be monitored by a navigator includes a myocardial tissue boundary making up a cardiac muscle wall, or a major artery or vein having motion induced by blood pressure waves imparted by the beating heart. These are merely illustrative examples.

The gating device (e.g. MR controller 30 and ancillary components) determines the gating time offset by operating the MR imaging device 10 to repeatedly execute the navigator pulse sequence 40 to generate navigator data in image space as a function of time. A motion signal 44 of an anatomical feature as a function of time is extracted 42 from the navigator data. For example, in the case of a feature comprising the thoracic diaphragm boundary, the operation 42 may include identifying this boundary as a steep intensity gradient in each 2D or 3D navigator image (or each 1D navigator data set in image space, in the case of a 1D pencil beam navigator), and the position of this boundary is plotted as a function of time for the time sequence of images or 1D navigator data sets to produce the motion signal 44. Concurrently with operating the MR imaging device 10 to repeatedly execute the navigator sequence 40, a concurrent physiological signal 16 as a function of time is generated by the physiological monitor 12, 14. This is straightforward since the physiological monitor 12 (e.g. air-filled belt) is designed to operate with the patient loaded into the MR imaging device 10 in order to provide the gating signal; thus, the same physiological monitoring is performed during the repeated execution of the navigator pulse sequence 40 to generate the concurrent physiological signal 16. A gating time offset 50 is then determined by comparing the motion signal 44 of the anatomical feature as a function of time and the concurrent physiological signal 16 as a function of time. This gating time offset 50 is thereafter used in the gating. That is, the MR controller 30 operates the MR imaging device 10 to perform gated MR imaging (i.e. executing the gated MR imaging sequence 36) using gating times defined as occurrence times of gating events detected by the physiological monitor 12, 14 modified by the gating time offset 50.

In the illustrative example of FIG. 1, the gating time offset 50 is determined by comparing the signals 16, 44 as follows. An occurrence of the chosen gating event is identified in the physiological signal 16 in an operation 52. This may be done automatically, e.g. the gating event may be defined as the pressure maximum (or minimum) measured for the illustrative air-filled belt respiratory monitor and such maxima (or minima) are readily detected automatically in the pressure-versus-time waveform. Alternatively, the operation 52 may be performed manually, e.g. the pressure-versus-time waveform may be plotted and the MR operator manually selects the event using the mouse 28. Similarly, in an operation 54 an occurrence of a desired start of MR imaging data acquisition is identified in the motion signal 44. Again, this may be done either automatically or manually. For example, the motion signal 44 may be plotted as a function of time and the user selects the desired start on the plot of the motion signal 44 of the anatomical feature. Alternatively, the desired start may be selected automatically using some criterion, such as identifying the beginning of a quiescent period in which the motion is small. In the case of respiration, this usually corresponds to an end-expiration period, and it will be expected that the diaphragm (and hence its boundary) will have little motion during this period. The gating time offset 50 is then selected as a time difference between the time of the chosen gating event and the time of the desired start of MR imaging data acquisition.

It should be noted that gating can be performed either prospectively or retrospectively. In embodiments in which the gated MR imaging employs prospective gating, the MR imaging data acquisition is triggered at the gating times defined as occurrence times of gating events detected by the physiological monitor modified by the gating time offset 50. In this case, the gating time offset 50 should be a gating delay, i.e. the modification is to delay the start of MR imaging data acquisition by the gating time offset.

In the case of retrospective gating, MR imaging data are acquired continuously while recording the gating events detected using the physiological monitor 12, 14, and the collected imaging data are retrospectively gated using the recorded gating events modified by the gating time offset 50. The events are marked with the event times+offset as start point of acceptance windows to validate or invalidate respective data and track the data measured until completion.

In a variant embodiment, the gating time offset 50 is determined automatically in an operation 56 by computing a time shift between the two signals 16, 44. This approach recognizes that both the physiological signal 16 and the motion signal 44 are expected to be at least quasiperiodic (in the case of respiratory or cardiac gating) so that a phase shift can be defined between the two signals 16, 44. In this case, the phase shift is used as the gating time offset 50.

The foregoing are merely illustrative examples of some approaches for determining the gating time offset 50 by comparing the motion signal 44 of the anatomical feature as a function of time and the concurrent physiological signal 16 as a function of time. Moreover, the disclosed approaches are not mutually exclusive. For example, the approach of identifying 52 a trigger event in the physiological signal 16 and identifying 54 a desired start time in the motion signal 44 and taking the difference as the gating time offset 50 can be augmented by computing the time difference by correlation 56 in order to ensure the times identified in the operations 52, 54 are in the same respiratory cycle (or same cardiac cycle, et cetera). Other approaches are also contemplated. In general, the motion signal 44 of the anatomical feature as a function of time is leveraged to account for patient-specific or even imaging scan-specific variations in the time offset between the measured physiological signal (e.g. respiratory signal or cardiac signal) and the motion of the imaged anatomy produced by the physiological process (e.g. respiration or cardiac cycling).

In the illustrative examples herein, while a single electronic processor 20 is illustrated for brevity, it will be understood that the electronic processing disclosed herein may alternatively be embodied by a plurality of operatively interconnected electronic processors. For example, the MR controller 30 may be implemented as a dedicated electronic controller while the reconstruction/display 32 may be implemented by a different computer. It is also contemplated for the physiological monitor controller to be integrated with the electronic processor that controls the MR imaging device 10 and/or with the electronic processor that reconstructs and displays the MR images. Likewise, wherever herein the term "non-transitory storage medium" or the like is employed, it is to be understood that the storage medium may be a single storage medium or may include a plurality of storage media. For example, it is contemplated to store the instructions executed by the MR controller 30 on a different storage medium from the storage medium that stores the imaging and navigator sequences 36, 40.

Figure 2:
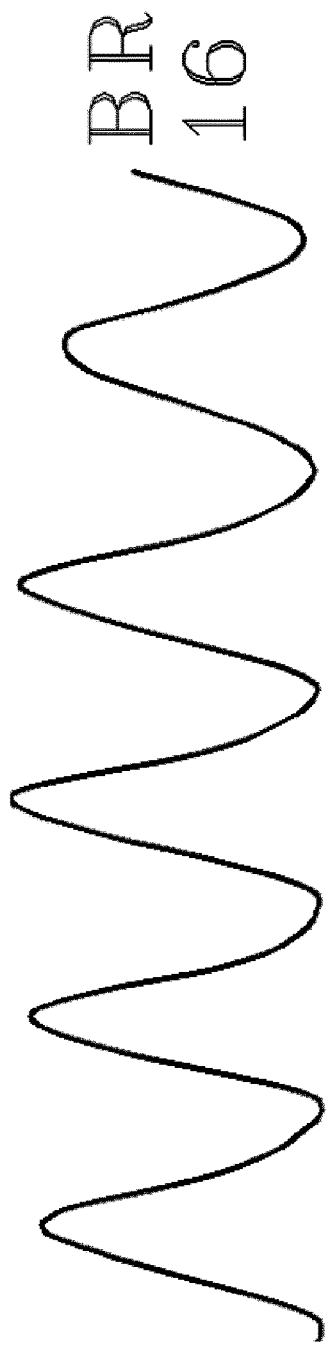
FIG. 2 diagrammatically illustrates a respiratory monitor waveform as a function of time.
Figure 3:
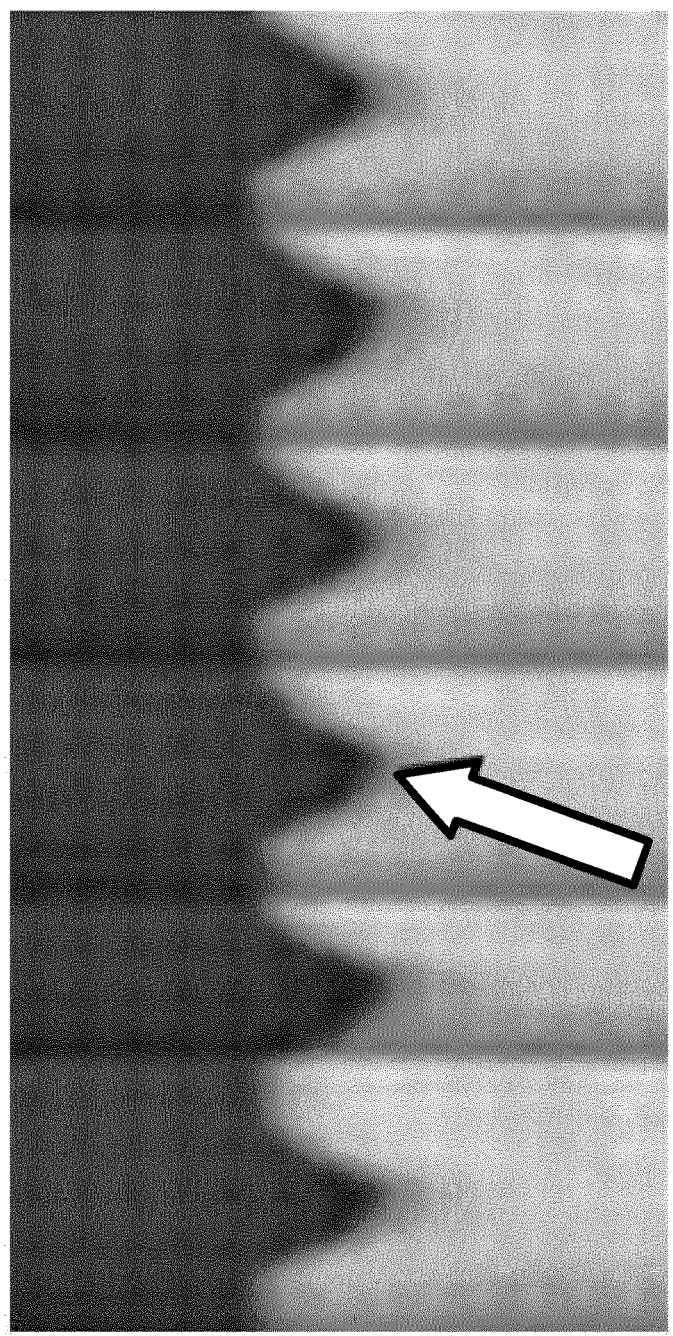
FIG. 3 diagrammatically illustrates a navigator feature waveform as a function of time.
Figure 4:
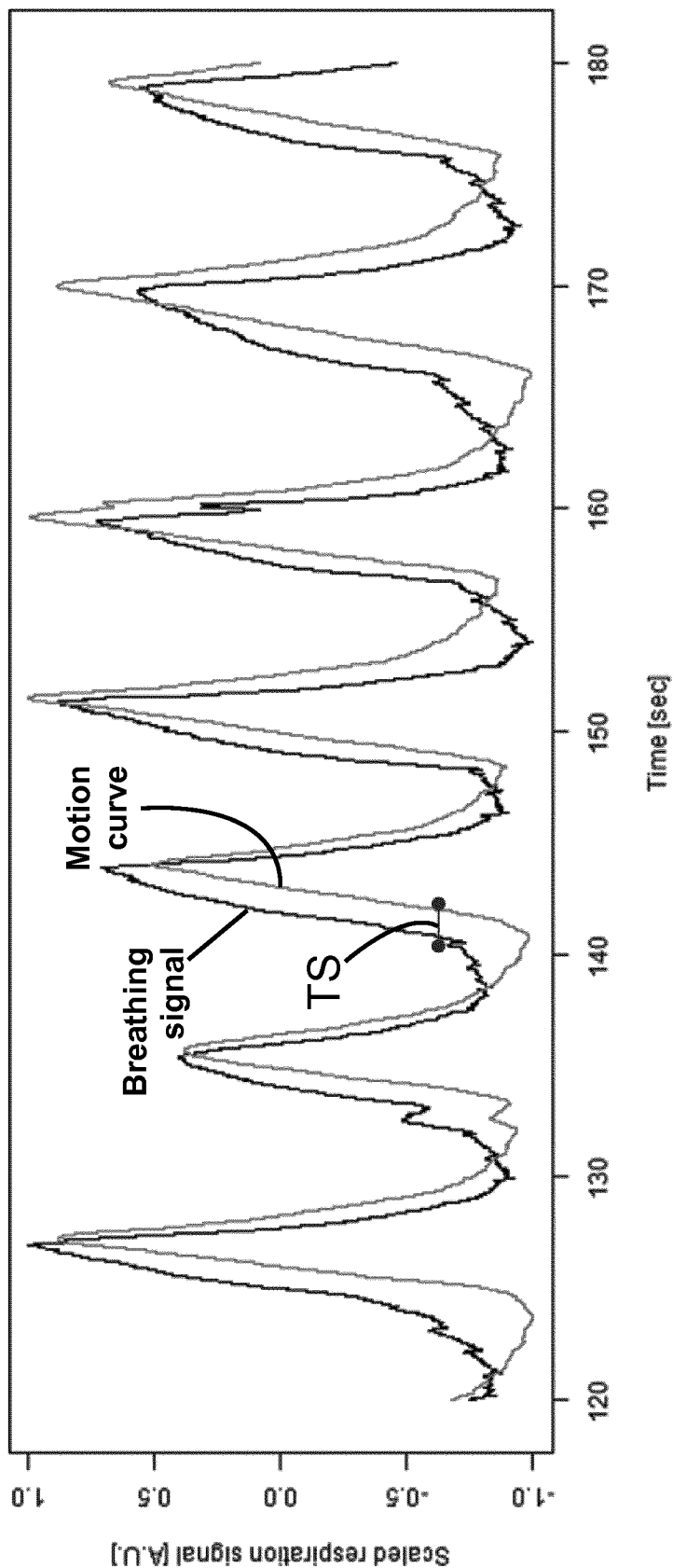
FIG. 4 diagrammatically illustrates respiratory monitor and navigator feature waveforms plotted together, with certain salient measurements indicated.

With reference now to FIGS. 2-4, a more specific illustrative example is presented, relating to respiratory-gated MR imaging. In this example, at the beginning of the imaging exam, the navigator (1D, 2D or 3D) signal is acquired using the MR imaging device 10 repeatedly executing the navigator pulse sequence 40. The navigator is positioned (either manually, e.g. using scout scans, or automatically) at the location of the target moving structure (i.e., the anatomical feature whose motion is tracked). Real-time navigator images of the moving anatomical feature over a few respiratory or cardiac cycles (or other physiological cycle used for the gating) are acquired. The motion curve 44 representative of the main motion direction is computed 42 from the navigator images using image analysis techniques, e.g. edge detection, region segmentation, or so forth. Simultaneously, the physiology signal 16 measured by the physiology sensor 12, 14 is acquired. In this example, the gating time offset 50 is determined as follows. The mean (or median) shift between the two signals 16, 44 is computed (operation 56), for example based on maximizing the correlation between these two signals. The motion state of the internal organ which is desired for imaging (e.g. end-expiration or end-inspiration) is defined (operations 52, 54), either manually by the operator or automatically based on some pre-settings. This may be done, for example, manually using a graphical user interface. The gating time offset 50 is computed based on the mean shift and the position of the desired motion state within one respiration cycle (for the illustrative example of respiratory gating). FIG. 2 illustrates a suitable example of the physiological signal 16, here embodied as a breathing signal determined from analyzing movement of a shadow of the chest on a wall of a magnet bore of the MR imaging device 10. (By contrast, in the embodiment of FIG. 1, this breathing signal is provided by the air-filled belt 12). FIG. 3 illustrates the motion curve 44 of an anatomical feature, namely the liver dome in the illustrative example of FIG. 3, due to breathing measured by a 1D pencil beam navigator sequence over the same respiratory cycles that produced the breathing signal of FIG. 2. In FIG. 3, the arrow shows the motion state at the desired start of imaging data acquisition. FIG. 4 illustrates display of both signals 16, 44 plotted against a common time axis. In FIG. 4, the mean or median time shift TS between these two curves 16, 44 is indicated by a time shift determined by maximizing the cross-correlation between these two curves. As the signals 16, 44 are (quasi-)periodic, this time shift can also be thought of as a phase shift between the motion signal 44 of the anatomical feature and the concurrent physiological signal 16.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A gating device for a magnetic resonance (MR) imaging device, the gating device comprising:
a physiological monitor;
an electronic processor; and
a non-transitory storage medium storing a navigator pulse sequence, a gated MR imaging sequence, and instructions readable and executable by the electronic processor to perform a gated MR imaging method including:
operating the MR imaging device to repeatedly execute the navigator pulse sequence to generate navigator data in image space as a function of time;
extracting a motion signal of an anatomical feature as a function of time from the navigator data;
concurrently with operating the MR imaging device to repeatedly execute the navigator pulse sequence, acquiring a concurrent physiological signal as a function of time generated by the physiological monitor;
computing a time corresponding to a phase shift between the motion signal of the anatomical feature as a function of time and the concurrent physiological signal as a function of time;
determining a gating time offset based on the computed time corresponding to the phase shift between the motion signal of the anatomical feature and the concurrent physiological signal; and
operating the MR imaging device to perform the gated MR imaging sequence using gating times defined as occurrence times of gating events detected by the physiological monitor modified by the gating time offset.

2. The gating device of claim 1 further comprising:
a display; and
a user input device,
wherein the gated MR imaging method further includes:
operating the display to plot the motion signal of the anatomical feature and the concurrent physiological signal against a common time axis;
receiving a user input via the user input device indicating a gating event on the plot of the concurrent physiological signal;
receiving a user input via the user input device indicating a desired start of MR imaging data acquisition on the plot of the motion signal of the anatomical feature; and
computing the gating time offset based on a time difference between the indicated gating event and the indicated desired start of MR imaging data acquisition.

3. The gating device of claim 1 wherein the gated MR imaging employs prospective gating in which MR imaging data acquisition is triggered at the gating times.

4. The gating device of claim 1 wherein the gated MR imaging employs retrospective gating in which MR imaging data are acquired continuously while recording the gating events detected using the physiological monitor and retrospectively gated using the recorded gating events modified by the gating time offset.

5. The gating device of claim 1 wherein the physiological monitor comprises a respiratory monitor and the gated MR imaging is respiratory-gated MR imaging.

6. The gating device of claim 5 wherein the extracting comprises:
extracting a motion signal of a thoracic diaphragm boundary as a function of time from the navigator data.

7. The gating device of claim 1 wherein the physiological monitor comprises an electrocardiograph (ECG) and the gated MR imaging is ECG-gated MR imaging.

8. The gating device of claim 1 wherein the navigator pulse sequence is a pencil beam navigator, and operating the MR imaging device to repeatedly execute the navigator pulse sequence generates a time sequence of one-dimensional (1D) navigator data sets in image space.

9. The gating device of claim 1 wherein the navigator pulse sequence is a two- or three-dimensional (2D or 3D) navigator pulse sequence and operating the MR imaging device to repeatedly execute the 2D or 3D navigator pulse sequence generates a time sequence of 2D or 3D images.

10. A non-transitory storage medium storing:
a navigator pulse sequence;
a gated magnetic resonance (MR) imaging sequence; and
instructions readable and executable by an electronic processor to perform a gated MR imaging method comprising:
operating an MR imaging device to repeatedly execute the navigator pulse sequence to generate navigator data in image space as a function of time;
extracting a motion signal of an anatomical feature as a function of time from the navigator data;
concurrently with operating the MR imaging device to repeatedly execute the navigator pulse sequence, acquiring a concurrent respiratory or cardiac cycling signal as a function of time generated by a respiratory or cardiac monitor;
computing a time corresponding to a phase shift between the motion signal of the anatomical feature and the concurrent respiratory or cardiac cycling signal;
determining a gating time offset based on the computed time; and
operating the MR imaging device to perform the gated MR imaging sequence using gating times defined as occurrence times of gating events detected by the respiratory or cardiac monitor modified by the gating time offset.

11. The non-transitory storage medium of claim 10 wherein the gated MR imaging method further includes:
operating a display to plot the motion signal of the anatomical feature and the concurrent respiratory or cardiac signal against a common time axis.

12. The non-transitory storage medium of claim 10 wherein the gated MR imaging method further includes:
receiving identification of, or automatically identifying, a gating event in the concurrent respiratory or cardiac signal;
receiving identification of, or automatically identifying, a desired start of MR imaging data acquisition in the motion signal of the anatomical feature; and
computing the gating time offset based on a time difference between the gating event and the desired start of MR imaging data acquisition.

13. The non-transitory storage medium of claim 10 wherein the gated MR imaging employs one of:
prospective gating in which MR imaging data acquisition is triggered at the gating times; and
retrospective gating in which MR imaging data acquisition is acquired continuously while recording the gating events detected using the respiratory or cardiac monitor and retrospectively gated using the recorded gating events modified by the gating time offset.

14. The non-transitory storage medium of claim 10 wherein extracting the motion signal comprises:
extracting a motion signal of an organ boundary as a function of time from the navigator data.

15. The non-transitory storage medium of claim 10 wherein one of:
the navigator pulse sequence is a pencil beam navigator and operating the MR imaging device to repeatedly execute the navigator pulse sequence generates a time sequence of one-dimensional (1D) navigator data sets in image space;
the navigator pulse sequence is a two-dimensional (2D) navigator pulse sequence and operating the MR imaging device to repeatedly execute the 2D navigator pulse sequence generates a time sequence of 2D images; or
the navigator pulse sequence is a three-dimensional (3D) navigator pulse sequence and operating the MR imaging device to repeatedly execute the 3D navigator pulse sequence generates a time sequence of 3D images.

16. A gated magnetic resonance (MR) imaging method comprising:
repeatedly executing a navigator pulse sequence using an MR imaging device to generate navigator data in image space as a function of time;
extracting a motion signal of an anatomical feature as a function of time from the navigator data;
concurrently with operating the MR imaging device to repeatedly execute the navigator pulse sequence, acquiring a concurrent respiratory cycling signal as a function of time generated by a respiratory monitor;
computing a time corresponding to a phase shift between the motion signal of the anatomical feature and the concurrent respiratory cycling signal;
determining a gating time offset based on the computed time; and
operating the MR imaging device to perform a gated MR imaging sequence using gating times defined as occurrence times of gating events detected by the respiratory monitor modified by the gating time offset.

17. The gated MR imaging method of claim 16 wherein the anatomical feature is an organ boundary.

18. The gated MR imaging method of claim 16 wherein the time corresponding to the phase shift includes:
computing a time difference between a gating event in the respiratory cycling signal and a reference point in the motion signal of the anatomical feature.

* * * * *